(12) United States Patent
Rabin et al.

(10) Patent No.: US 9,724,536 B1
(45) Date of Patent: Aug. 8, 2017

(54) EMBEDDED FIBER PHOTOTHERAPY LIGHT CAP

(71) Applicants: Michael I. Rabin, Gates Mills, OH (US); David A. Smith, Gates Mills, OH (US)

(72) Inventors: Michael I. Rabin, Gates Mills, OH (US); David A. Smith, Gates Mills, OH (US)

(*) Notice: Subject to any disclaimer, the term of this patent is extended or adjusted under 35 U.S.C. 154(b) by 49 days.

(21) Appl. No.: 14/693,561

(22) Filed: Apr. 22, 2015

Related U.S. Application Data

(60) Provisional application No. 61/982,776, filed on Apr. 22, 2014.

(51) Int. Cl.
*A61N 5/067* (2006.01)
*A61N 5/06* (2006.01)
*G02B 6/42* (2006.01)

(52) U.S. Cl.
CPC .......... *A61N 5/0617* (2013.01); *G02B 6/429* (2013.01); *A61N 2005/063* (2013.01); *A61N 2005/067* (2013.01); *A61N 2005/0626* (2013.01); *A61N 2005/0647* (2013.01); *A61N 2005/0651* (2013.01); *A61N 2005/0665* (2013.01)

(58) Field of Classification Search
CPC .... A61N 5/0617; A61N 5/0616; A61N 5/067; A61N 2005/0626; A61N 2005/0627; A61N 2005/0628; A61N 2005/0642; A61N 2005/0643; A61N 2005/0647; A61F 2007/0002; A61F 2007/0007; A61F 2007/0008

USPC ............... 607/88–91, 96, 108–110; 128/898
See application file for complete search history.

(56) References Cited

U.S. PATENT DOCUMENTS

| | | | | |
|---|---|---|---|---|
| 6,050,990 A | * | 4/2000 | Tankovich | A61B 18/203 606/16 |
| 2004/0153131 A1 | * | 8/2004 | Yorke | A61N 5/0617 607/91 |
| 2009/0036845 A1 | * | 2/2009 | Smith | A61M 35/00 604/289 |
| 2010/0106077 A1 | * | 4/2010 | Rabin | A61N 5/0616 604/20 |
| 2010/0242155 A1 | * | 9/2010 | Carullo, Jr. | A61N 5/0617 2/171.2 |
| 2011/0218598 A1 | * | 9/2011 | Shanks | A61N 5/0617 607/89 |
| 2015/0297914 A1 | * | 10/2015 | Hamid | A61N 5/0617 607/89 |
| 2016/0045763 A1 | * | 2/2016 | Tapper | A61N 5/0617 607/91 |

* cited by examiner

*Primary Examiner* — Ahmed Farah
(74) *Attorney, Agent, or Firm* — K. David Crockett, Esq.; Paul J. Backofen, Esq.; Crockett & Crockett, PC

(57) ABSTRACT

A phototherapy device includes a high intensity light source secured to a leaky light conducting fiber to leak light along the length of the fiber. The light fiber is illuminated at either or both ends by the light source and the light fiber is generally oriented in a 3-D spiral pattern to form a dome of light to provide phototherapy to an area of a patient's scalp to be treated. A generally hemispherical shell is formed of a first or inner translucent diffuser layer secured to a second or outer reflective layer, the first and second layers encapsulating the 3-D non-overlapping spiral pattern light fiber. A control system is also provided to turn off the light source when a break or discontinuity occurs in the fiber.

4 Claims, 4 Drawing Sheets

EMBEDDED FIBER PHOTOTHERAPY LIGHT CAP

RELATED APPLICATIONS

This application claims priority to U.S. Provisional Patent Application 61/982,776 filed Apr. 22, 2014.

FIELD OF THE INVENTIONS

The inventions described below relate to the field of hair growth and regeneration in a human scalp.

BACKGROUND OF THE INVENTIONS

There is a substantial body of evidence supporting phototherapy for promoting human hair growth and regrowth. Additional evidence exists that low-level light therapy (LLLT) may be most beneficial if provided within one or more narrow spectral windows.

At least three US manufacturers sell products that deliver red light to the scalp: Sunetics, HairMax and Laser Hair Therapy. Prior art methods of dosing include "laser" combs using LEDs or laser diodes which must be slowly scanned across the scalp or full-head hoods similar in appearance and dimensions to the classic hair salon hair dryer hood which deliver red light to the head, usually in a doctor's office setting.

Conventional phototherapy regimens generally require the patient to administer the therapy, either by applying the light themselves, region by region with a light comb or by sitting under a hood in a medical or salon setting. There is a potential risk to the patients from the intense laser light leaking from an unconnected light source or from the housing into the patient's eyes.

SUMMARY

The devices and methods described below provide for a portable phototherapy apparatus that includes a high intensity light source secured to a leaky light conducting fiber to leak light along the length of the fiber and a control system to turn off the light source when a break or discontinuity occurs in the fiber. The light fiber is illuminated at either or both ends by the light source and the light fiber is generally oriented in a 3-D spiral pattern to form a dome of light to provide phototherapy to an area of a patient's scalp to be treated. A generally hemispherical, cranial-shaped shell is formed of a first or inner translucent layer secured to a second or outer reflective layer, the first and second layers encapsulate the 3-D spiral pattern light fiber.

The control system incorporates a microprocessor and is operatively connected to a photodetector at one or both ends of the light fiber and the control system is programmed to turn off the light source if the fiber is broken or disconnected from the light source. Alternatively, if the light is applied to only a first end of the light fiber, the photodetector may be secured to the first end of the light fiber along with the light source, and the second end of the light fiber may include a mirror to reflect light back along the fiber to the photodetector. If the fiber is broken, it will not transmit the expected level of light throughout its length, but instead will emit light at the point of breakage. There will insufficient light incident on the photodetector and the control system will turn off the light source. Thus, the control system is programmed to prevent delivery of high energy light from a broken fiber or any other system component. An interlock is also provided to prevent the light source from turning on if one or both ends of the light fiber are not connected to the light source.

An optional colloid solution may be enclosed within the shell with the light fiber to scatter the light leaking from the fiber to the area to be treated. The colloid solution may be formulated to support convection within the solution to generate fluctuating illumination on the scalp to be treated. The colloid solution may also include reflective and refractive elements that operate with the moving colloid solution to optimize the fluctuating illumination on the scalp to be treated.

The light source may be any suitable source of light such as a laser, LED, or other source. The light may be coherent or non-coherent and may consist of one or more selected frequencies or combinations of frequencies of visible, infrared or ultraviolet light.

The phototherapy device includes a generally hemispherical, cranial shaped shell and an optical fiber wrapped to form a non-overlapping three dimensional shape and embedded within the generally hemispherical shell. The optical fiber has a first end for connecting to a light source and a second end having a reflector. A control system is operatively connected to a photodetector and the light source, both of which are operatively connected to the optical fiber. A microprocessor is included in the control system and the microprocessor is programmed to control operation of the light source and the photodetector to monitor light reflected from the reflector and provide a signal corresponding to the intensity of the reflected light to the microprocessor.

The phototherapy device may instead be constructed with a photodetector at the second end, and may include light sources at both ends and a photodetector at both ends. This phototherapy device, as described above, includes a generally hemispherical shell and an optical fiber wrapped to form a non-overlapping three dimensional shape and embedded within the generally hemispherical shell. The optical fiber has a first end and a second end with both ends extending from the shell. In this embodiment, light sources and sensors operably connected to the control system are connected to both ends of the optical fiber with a first laser diode optically coupled to the first end of the optical fiber and a second laser diode optically coupled to the second end of the optical fiber and a microprocessor in the control system is programmed to control operation of the laser diodes. At least one photodetector is optically coupled to the optical fiber to monitor light emitted from the optical fiber at the end of the optical fiber and provide a signal corresponding to the intensity of that emitted light to the microprocessor.

An optional generally hemispherical, cranial shaped liner may be oriented between the shell and the area to be treated on the patient's scalp. The liner includes a plurality of spacers or light guiding projections that contact and or adhere to the scalp to guide light emitted from the inner translucent shell layer without loss from scalp reflection or hair blockage and can also be hollow to guide any suitable therapeutic liquid or to accommodate a specialized transdermal patch. Similarly, the light guiding projections may be filled with or formed of any material having suitable light guiding properties.

DETAILED DESCRIPTION OF THE INVENTIONS

Figures 1, 2:
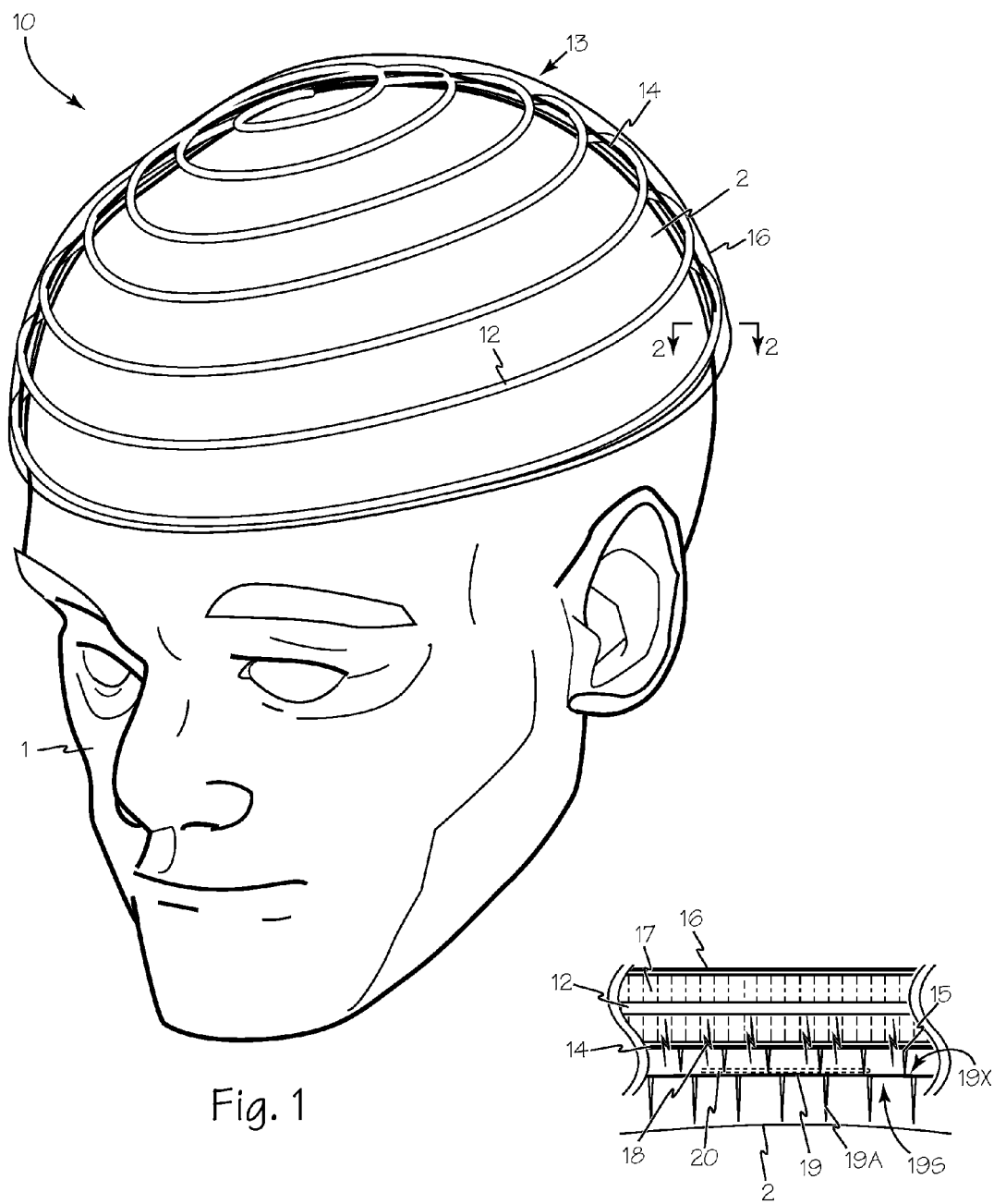
FIG. 1 is a perspective view of an embedded fiber phototherapy light cap and liner on the head of a user.
FIG. 2 is a cross section of a portion of the embedded fiber phototherapy light cap and liner of FIG. 1 taken along 2-2.

FIGS. 1 and 2 illustrate user 1 with embedded fiber phototherapy light cap 10 covering scalp area to be treated 2. Phototherapy light cap 10 includes leaky optical fiber 12 oriented in a non-overlapping 3-D pattern to form a generally hemispherical shape. Optical fiber 12 is enclosed within generally hemispherical, cranial-shaped shell 13 which is formed of first or inner transparent or translucent diffuser layer 14 secured to second or outer reflective layer 16. First and second layers 14 and 16 form a shell which encapsulates light fiber 12 along with optional colloid solution 17 to scatter light 18 leaking from fiber 12 to scalp area 2 to be treated. First layer 14 may also includes spacers 15 to provide a uniform distance between the first layer and scalp area 2. A light source is coupled to a first end of fiber 12 and a control system is programmed to control the light source in response to a signal corresponding to the intensity of light reflected from a mirror on the second end of fiber 12.

Optional internal liner 19 is a generally hemispherical diffuser disposed between embedded fiber phototherapy light cap 10 and scalp 2 to improve the uniformity of illumination on the scalp. Liner 19 may include spacers 19A extending from inner surface 19S to provide a uniform offset from scalp 2 and optimize the uniformity of illumination arriving at scalp 2.

Alternatively, spacers 19A may be configured to conduct a portion of the coherent light impinging on outer surface 19X directly to scalp 2 bypassing any hair that is present. Light guiding spacers 19A may adhere to the scalp using any suitable technique and they may also be hollow to enable conduction of therapeutic solutions from a transdermal patch 20 through projections 19A directly to the scalp.

Figure 3:
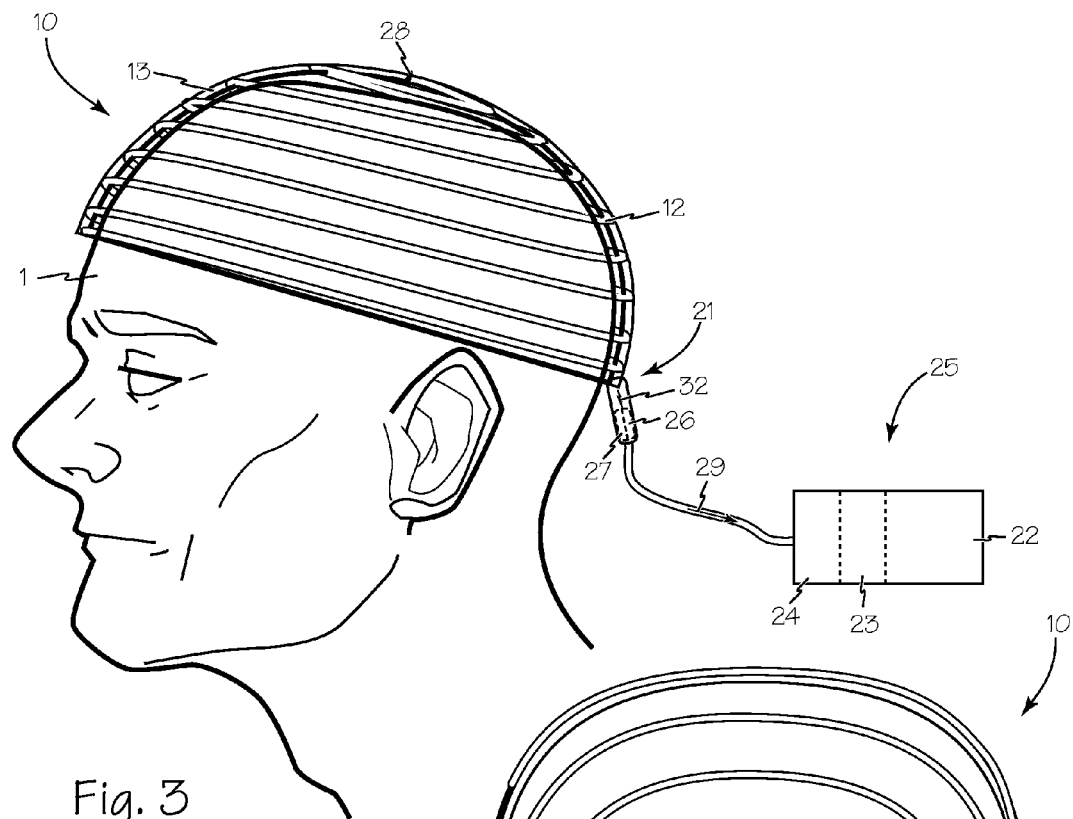
FIG. 3 is a side view of the embedded fiber phototherapy light cap, liner and user of FIG. 1 illustrating the light source and connector.

FIG. 3 is a side view of embedded fiber phototherapy light cap 10 connected to light source 21. Light source 21 couples to leaky fiber 12. Battery 22 and laser driver electronics 24 are operatively connected to microprocessor 23 in control system 25. Driver electronics 24 is operably connected to laser diode 26. A photodetector or light sensor such as light sensor 27 is also operably connected to leaky fiber 12 to detect the intensity of light reflected from mirror 28 which terminates leaky fiber 12. Light sensor 27 produces an output signal, light safety signal 29, which represents the intensity of the light incident on the sensor. Light safety signal 29 is applied to microprocessor 23. The control system is operable to receive the light safety signal, which is a signal corresponding to the level of light detected by the light sensor. Control system 25 is programmed to initiate, adjust or terminate the application of power to the light source 21 according to light safety signal 29 received by microprocessor 23. The control system is preferably programmed to terminate application of power to the light source if the light safety signal is indicative of a light level which is significantly lower that the level of light expected to be reflected by the mirror and subsequently transmitted through the leaky fiber to the photodetector. More generally, the control system is programmed to control the light source in response to the signal corresponding to the intensity of the reflected light.

Figure 4:
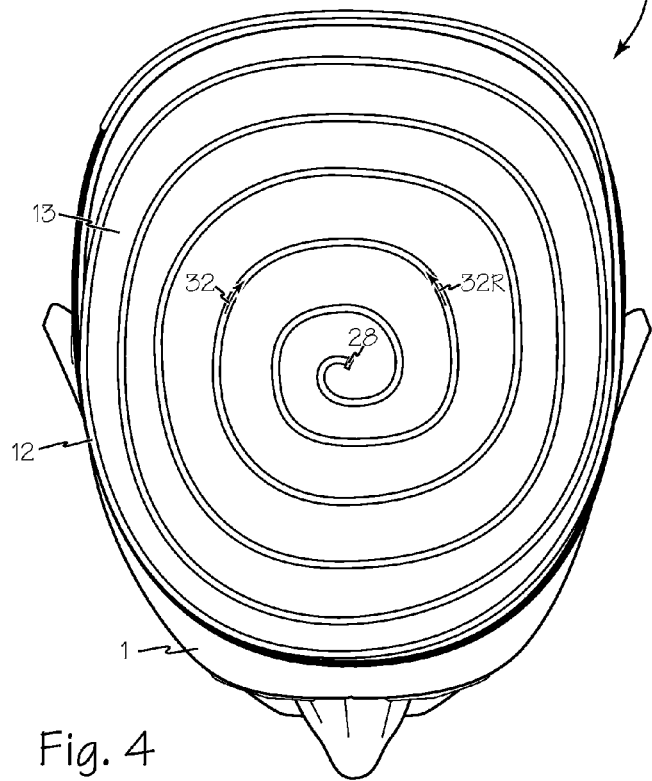
FIG. 4 is a top view of the embedded fiber phototherapy light cap, liner and user of FIG. 1.

FIG. 4 is a top view of embedded fiber phototherapy light cap 10 oriented for use on user 1. The non-overlapping 3-D pattern of fiber 12 is shown enclosed in shell 13. Fiber 12 may be terminated with mirror 28 or with a photodetector operably connected to control system 25. Light sensor/photodetector 27 enables implementation of a safety interlock which prevents high energy laser light from being discharged if the light source is not connected to fiber 12 or if fiber 12 is broken or cracked. Light 32 generally is coupled into fiber 12. Light 32 travels the length of the fiber, a portion of the light is scattered through the length of fiber 12 and any light not scattered or leaked out of the fiber on its first pass through the fiber is reflected back along the fiber by mirror 28 enabling additional light to leak from the fiber in the reflected pass. Return light 32R is then received by light sensor/photodetector 27. The output from light sensor 27 is applied to microprocessor 23, and as long as the intensity of return light 32R exceeds a preset limit, laser diode 26 remains on.

Figure 5:
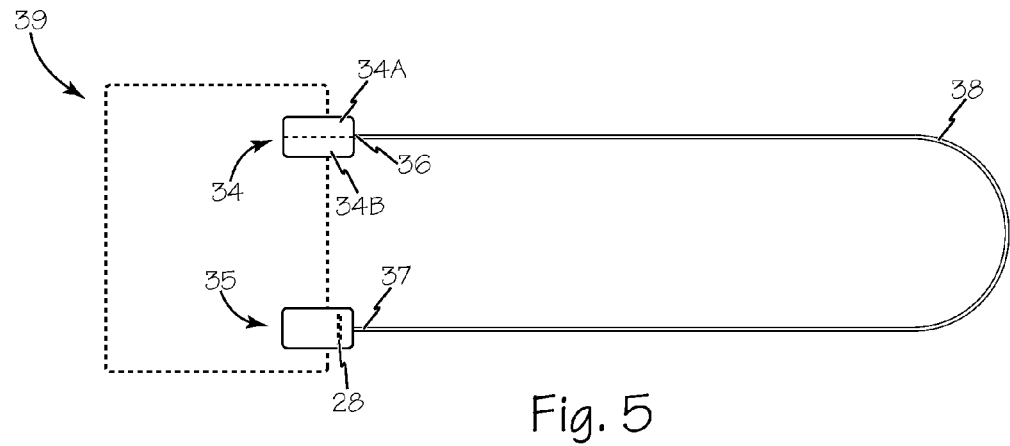
FIG. 5 is a block diagram of an alternate fiber/control system configuration.

Alternatively, a fiber such as fiber 12 may be folded and wrapped to permit first end 36 and second end 37 of fiber 38 to operably connect to control system 39 as shown in FIG. 5. This configuration permits light to be injected from either or both ends of the fiber. Each end of fiber 12 is attached to a coupling element which may be a combination of laser diode and photodetector sensor, a laser diode, a mirror or any suitable combination. For example, first coupling element 34 includes laser diode 34A and photodetector 34B, both of which are operably coupled to fiber 38 and second coupling element 35 includes mirror 28. In an alternate configuration, first coupling element 34 may include a photodetector such as light sensor/photodetector 27 operably coupled to fiber first end 36 and second coupling element 35 may include a laser diode such as laser diode 26 operably coupled to fiber second end 37. The first and second coupling elements 34 and 35 may also include a laser diode and photodetector operably coupled to first and second fiber ends 36 and 37 respectively. If either photodetector senses a drop in the light emitted to the photodetector, one or both lasers are turned off by the microprocessor in the control system.

Figure 6:
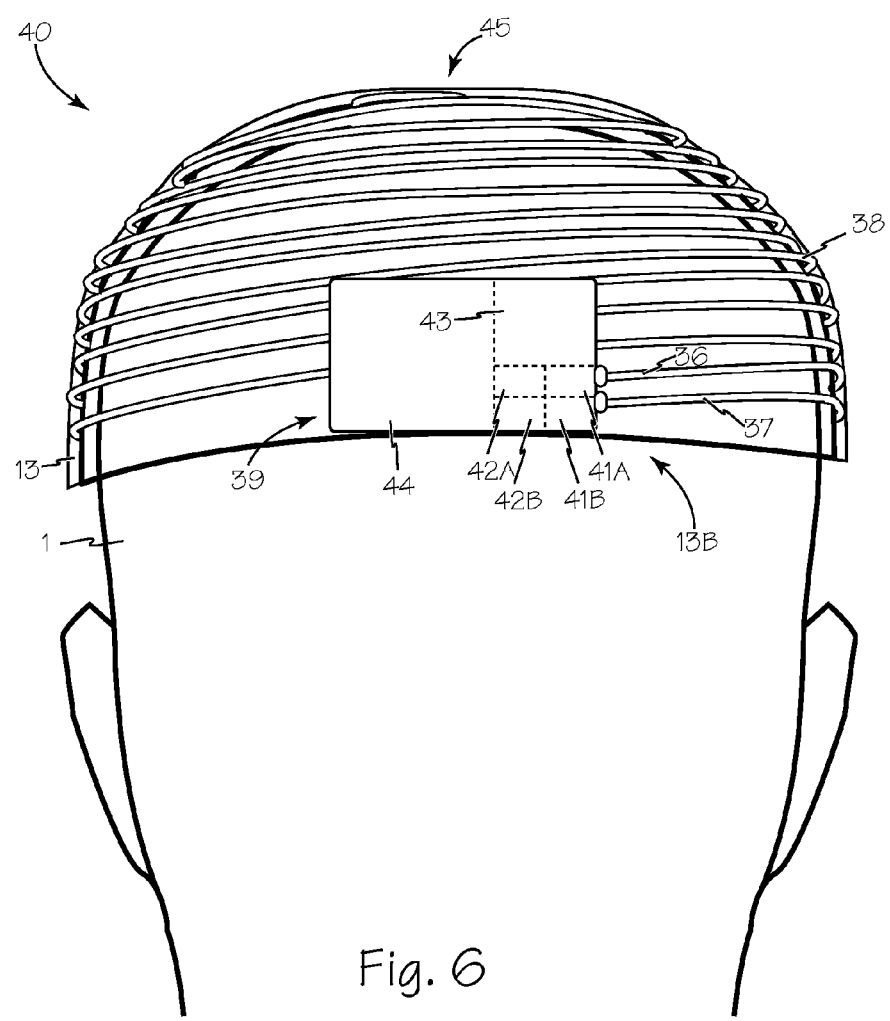
FIG. 6 is a back view of an embedded fiber phototherapy light cap with an alternate fiber wrap and the control system secured to the shell.

FIG. 6 illustrates a back view of embedded fiber phototherapy light cap 40 oriented for use on user 1. Phototherapy light cap 40 includes a single fiber 38 which extends from control system 39 to crown 45 and back down to control system 39. Control system 25 may be secured to back edge 13B of shell 13 as shown. Control system 39 is operatively connected to laser diodes 41A and 41B, each of which is combined with photo detectors 42A and 42B respectively. Each photodetector/diode module is optically connected to either first end 36 or second end 37 of fiber 38. Microprocessor 43 in the control system monitors the status of battery 44, the output of photo detectors 42A and 42B to determine if the laser diodes 41A and 41B are connected to fiber 38 and are safe to turn on or leave on.

Figure 7:
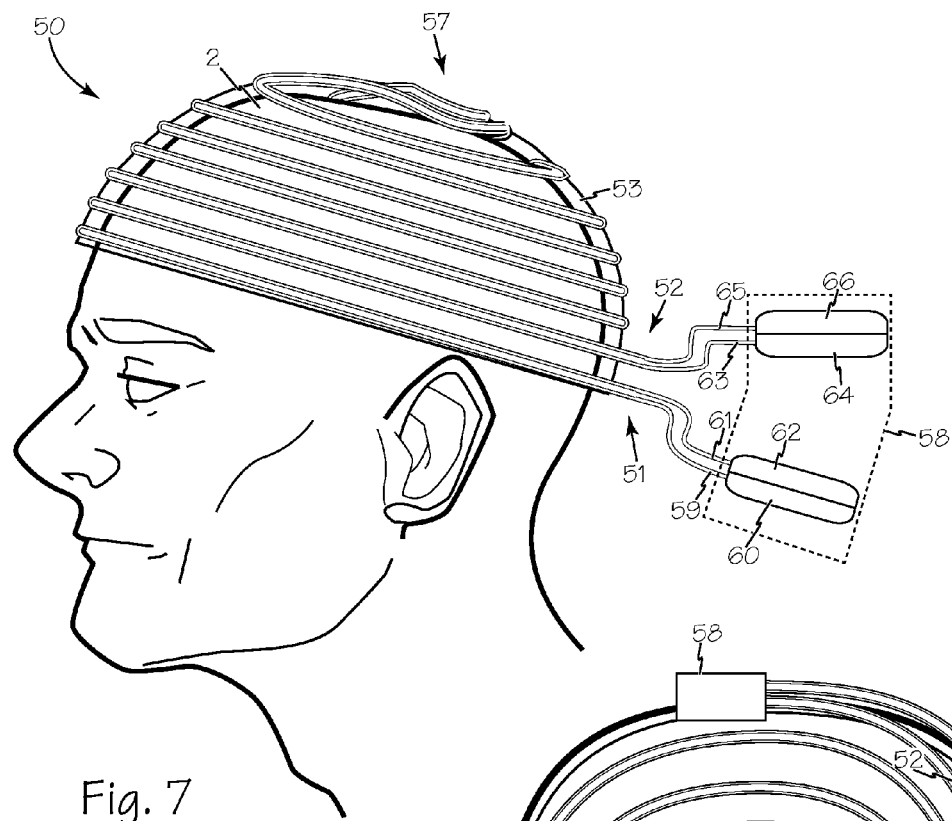
FIG. 7 is a side view of an alternate embedded fiber phototherapy light cap with folded fibers.
Figure 8:
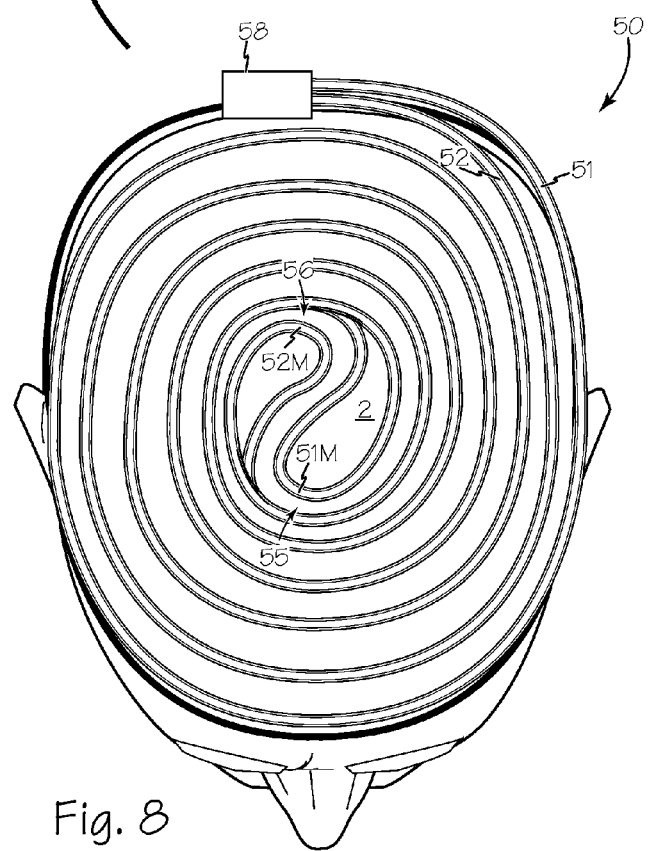
FIG. 8 is a top view of the alternate embedded fiber phototherapy light cap of FIG. 7.

FIGS. 7 and 8 illustrate an embedded fiber phototherapy light cap with folded fibers. Light cap 50 includes first fiber 51 and second fiber 52 enclosed within generally hemispherical shell 53 as discussed above. First and second fibers 51 and 52 are folded at their respective midpoints 51M and 52M with small radius bends 55 and 56 respectively which are generally oriented adjacent crown 57.

Control system 58 engages the two ends of each fiber. For example, input end 59 of first fiber 51 is coupled to laser 60 and second end 61 of first fiber 51 is coupled to a mirror or to a combination of mirror and photodetector such as mirror/photodetector 62. Input end 63 of second fiber 52 is coupled to laser 64 and second end 65 of second fiber 52 is coupled to a mirror or to a combination of mirror and photodetector such as mirror/photodetector 66. Phototherapy light caps may include one or more fibers and each fiber may or may not be folded as discussed above.

Alternatively, a phototherapy device may be configured as a two-dimensional apparatus with one or more leaky fibers arranged in one or more two-dimensional layers coupled to a control system as discussed above.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A phototherapy device comprising:
   a hemispherical shell;
   an optical fiber wrapped to form a three dimensional shape and embedded within the hemispherical shell, the optical fiber having a first end and a second end;
   a laser diode optically coupled to the first end of the optical fiber;
   a reflector disposed at the second end of the optical fiber, aligned to reflect light incident upon the reflector at the second end of the optical fiber toward the first end of the optical fiber;
   a photodetector optically coupled to the optical fiber to monitor light reflected from the reflector and provide a signal corresponding to the intensity of the reflected light;
   a control system operably connected to the laser diode and the photodetector, operable to control the laser diode and operable to receive the signal corresponding to the intensity of the reflected light; and
   wherein the control system is programmed to control the laser diode in response to the signal corresponding to the intensity of the reflected light.

2. The phototherapy device of claim 1 wherein the optical fiber is wrapped to form a non-overlapping three dimensional shape.

3. A phototherapy device comprising:
   a hemispherical shell;
   an optical fiber wrapped to form a three dimensional shape and embedded within the hemispherical shell, the optical fiber having a first end and a second end with both ends extending from the shell;
   a control system connected to both ends of the optical fiber;
   a first laser diode in the control system, the first laser diode optically coupled to the first end of the optical fiber;
   a second laser diode in the control system, the second laser diode optically coupled to the second end of the optical fiber;
   a microprocessor in the control system for controlling operation of the laser diodes; and
   at least one photodetector optically coupled to the optical fiber to monitor light emitted from the optical fiber and provide a signal corresponding to the intensity of the emitted light to the microprocessor.

4. The phototherapy device of claim 3 wherein the optical fiber is wrapped to form a non-overlapping three dimensional shape.

* * * * *